(12) United States Patent
Evans et al.

(10) Patent No.: US 6,498,247 B2
(45) Date of Patent: Dec. 24, 2002

(54) ALKALI OR ALKALINE EARTH METAL OF N-BUTYRIC ACID FOR TREATMENT OF COGNITIVE AND EMOTIONAL CONDITIONS

(75) Inventors: William T. Evans, Batesville, AR (US); Dwight L. McKee, Missoula, MT (US)

(73) Assignee: Pro-Health, Inc., Batesville, AR (US)

( * ) Notice: Subject to any disclaimer, the term of this patent is extended or adjusted under 35 U.S.C. 154(b) by 0 days.

(21) Appl. No.: 09/834,173

(22) Filed: Apr. 12, 2001

(65) Prior Publication Data

US 2002/0048612 A1 Apr. 25, 2002

Related U.S. Application Data

(60) Provisional application No. 60/196,813, filed on Apr. 13, 2000.

(51) Int. Cl.[7] .......................... G08B 3/16; A01N 65/00
(52) U.S. Cl. ........................................ 536/65; 424/725
(58) Field of Search ................ 424/195.1, 725; 536/65

(56) References Cited

U.S. PATENT DOCUMENTS

| 4,721,716 A | 1/1988 | Neesby |
| 4,735,967 A | 4/1988 | Neesby |
| 5,563,173 A | 10/1996 | Yatsu et al. |
| 5,858,690 A | * 1/1999 | Faller ...................... 424/184.1 |
| 6,316,690 B1 | * 11/2001 | Fogarty ......................... 800/3 |
| 6,333,351 B1 | * 12/2001 | Wu et al. .................... 514/538 |

FOREIGN PATENT DOCUMENTS

| EP | 345 081 | 12/1989 |
| WO | WO 95/11699 | 5/1995 |

OTHER PUBLICATIONS

Balch et al. Prescription for Nutritional Healing; Avery Publishing, 1998, pp. 10–17.*

Bartholini, G (1985) GABA receptor agonists: pharmacological spectrum and thereapeutic actions. Medicinal Research Reviews, New York, NY, US, vol. 5, No. 1, Jan. 1, 1985 pp. 55–75.

* cited by examiner

Primary Examiner—Jon P. Weber
Assistant Examiner—Patricia Patten
(74) Attorney, Agent, or Firm—William J. Sapone; Coleman Sudol Sapone P.C.

(57) ABSTRACT

A composition and method for treating some symptoms associated with cognitive and emotional conditions wherein the composition comprises at least one butyrate alkali metal or alkaline earth metal salt of n-butyric acid, preferably, a mixture of calcium and magnesium butyrate.

26 Claims, No Drawings

ALKALI OR ALKALINE EARTH METAL OF N-BUTYRIC ACID FOR TREATMENT OF COGNITIVE AND EMOTIONAL CONDITIONS

TECHNICAL FIELD

This invention relates to a composition and method for treating the symptoms associated cognitive and emotional conditions such as those found in attention deficit disorder (ADD), attention deficit/hyper activity disorder (AD/HD), Tourette's Syndrome, some forms of autism, and other physiological conditions which manifest cognitive or emotional abnormalities.

BACKGROUND

It has been recognized that a significant number of children are persistently hyperactive and have an attention span so short that they have difficulty in school and in social interactions. For example, such children have difficulty in situations that require sustained attention such as listening to teacher instructions, working on class assignment alone or in groups, and in completing assignments that require concentration. This condition carries over into adulthood, and manifests itself in many ways. For example, various physiological and/or psychological conditions cause symptoms that manifest in low frustration tolerance with temper outbursts, bossiness, stubbornness, insistence that requests be met, mood lability and poor self esteem, among others.

There are no established diagnostic laboratory tests in the clinical assessment of ADHD, as it is not yet clear as to the cognitive deficit responsible for the abnormal mental processing exhibited in ADHD.

For many years, methylphenidate hydrochloride (RITALIN) has been used to treat ADD and/or ADHD. Ritalin is a mild stimulant that has undesirable side effects such as nervousness, insomnia, hypersensitivity, anorexia, nausea, among others. Ritalin and other stimulants also do not relieve the often encountered excessive emotional response as they do not generate the emotional buffering or filtering necessary to delay and attenuate an excessive emotional response.

There are other physiological and/or psychological conditions that cause similar symptoms of uneasiness, restlessness, edginess, difficulty in concentration, recognition and memory deficiency, etc, requiring the use of prescription drugs such as WELLBUTRIN (1-(3-chlorophenyl)-2-[(1,1-dimethylethyl)amino]-1-propanone), which tend to cause side effects. Imipramine, desipramine, nortriptyline, amitriptyalin and cloripramine may also be used to treat symptoms such as associated with ADD/ADHD, excessive emotional response, etc. but these tricyclic drugs follow diverse mechanisms and tend to cause side effects. As these are normally chronic conditions, long term tolerance of the treatment is essential to successfully managing these symptoms. It is difficult for an individual to tolerate daily doses of a drug with even moderate side effects for life, yet that is what is presently required for theses individuals to function in society.

The search continues for a safe, effective and convenient treatment for the symptoms associated with diverse cognitive and emotional symptoms caused by conditions such as ADD and AHDH, for both adults and children, without the disadvantages and side effects found in the existing treatments.

SUMMARY OF THE INVENTION

It is an object of the present invention to provide a composition for the treatment and relief of the symptoms associated with conditions such as encountered with ADD or ADHD, and anxiety syndromes/conditions.

It is a further object to provide a method for treating the symptoms associated with various cognitive and/or emotional disorders such as ADD or ADHD.

It is yet another object to provide a method of treating the symptoms described above caused by diverse conditions, that is safe, effective and free of the side effects associated with prior treatments.

These and other objects of the present invention are achieved by a composition comprising at least one butyrate formulated preferably for oral administration, in a pharmaceutically acceptable carrier. Preferably, the butyrate is an alkali or alkaline earth metal salt of nbutyric acid, hereafter collectively termed the "butyrate". An example of the alkali metal salt may be the lithium, sodium or potassium butyrate, the alkaline earth salt may be calcium, magnesium or barium butyrate, or combinations thereof. Certain other butyrates may also be effective such as the ammonium or zinc butyrate, and thus the invention is not limited to those listed above.

The method comprises treating the symptoms of cognitive or emotional disorders, such as those described above relative to ADD/ADHD, though caused by any of a number of psychological and/or physiological conditions, by administrating an effective amount of a butyrate to a person in need of such treatment.

DETAILED DESCRIPTION OF THE INVENTION

The invention utilizes one or more alkali metal or alkaline earth metal salts of n-butyric acid in a pharmaceutically acceptable carrier. Preferably, one or more of the lithium, sodium, potassium, calcium, magnesium, zinc and barium butyrate is used.

In a preferred embodiment magnesium butyrate is used, though in another embodiment, a mixture of calcium and magnesium butyrate is used.

In a more preferred embodiment, the composition is formulated with one ore more optional ingredients such as antioxidants, antidepressants, memory promoters/enhancers, various vitamins, nutritional and herbal supplement that can be co-factors or otherwise enhance or synergize with the inventive compound and/or in the inventive treatment method.

The method of the invention comprises the administration of an effective amount of at least one butyrate, whether an alkali metal or alkaline earth metal, ammonium or zinc salt of 4-butyric acid. The salt may be selected from the group consisting of lithium, sodium, potassium, rubidium, cesium, beryllium, zinc, magnesium, calcium, strontium or barium, more preferably, sodium, potassium, magnesium and the calcium salts, most preferably the calcium and magnesium salts.

While any one salt may be used, it may be preferred to use a combination of salts such as a mixture of calcium and magnesium salts of 4-butyric acid, in a ratio of from 10:90 to 90:10 parts calcium to magnesium. More magnesium to calcium is preferred.

Butyric acid is a short claim fatty acid synthesized in the mammary glands. It is an oily liquid that has an unpleasant, rancid odor. It is produced by bacterial fermentation of unabsorbed carbohydrate in the colon and reaches concentrations of up to 20 mM in the colon and feces of animals and man. The other source of butyric acid is in the diet where it is present in low levels in many fruits and vegetables, but the best source is from milk fat, such as in butter, which contains 3–4% butyrate in a complex of glycerides or esters of glycerol butter fat. The calcium and magnesium butyrates apparently have no side effects when taken as a nutritional supplement and are classified as food by the Department of Agriculture. They are known for use as digestive aids and for desensitizing the gastrointestinal tract.

While alkali metal butyrates have been proposed for use in reducing food sensitivity, their use as agents for treating cognitive and emotional problems have not been recognized.

It is believed that the effectiveness of the proposed compounds relies on an increase in gamma amino butyric acid (GABA) in the brain, a well known inhibiting neurotransmitter. Thus, absorption of these compounds is believed to promote transfiguration into GABA, to raise the level of GABA in the brain. It is believed that these butyrates, or derivatives thereof formed in the blood stream, cross the blood brain barrier for conversion into GABA.

Preferably, one or more butyrates are formulated with promoters to enhance transformation to GABA. These may include, but are not limited to pyridoxine 5-phosphate, cyanocobalamin, folic acid, niacin and magnesium, which may be released from magnesium butyrate during the formation of GABA. L-glutamine, l-phenylalanine, l-tyrosine and l-taurine may also be included to promote dopamine, epinephrine, and norepinephrine formation, and to provide a calming effect.

Herbal supplements such as adaptogen including a medicinal mushroom cordyceps sinensis, could be used as it is a known moderator that enhances brain functions that are under active and calms down brain functions that are over active.

Phosphatidyl serine is an agent shown to have positive effects on short term memory and to treat symptoms associated with ADD/ADHD, and is complementary to the inventive composition. Pregnenolone is also a possible choice as a complementary compound, as is ginkgo biloba and/or the flavenols or oligomeric proanthocyanodins, known antioxidants, as well as the plant extract from huperzia serrata, a promoter for developing serotonin receptors on neurons.

Of course, many other compounds and ingredients can be formulated with the inventive compounds to enhance effectiveness or provide complementary beneficial effects in the treatment of cognitive and emotional disorders as discussed above.

The beneficial effects of the butyrate may be obtained by a dose level of about 200 to 3000 mg butyrate per day, preferably by oral supply of tablets containing from 200–1500 mg butyrate per capsule, the dose split into, for example, 2 tablets 3 times per day or 3 tablets, two times per day (500 mg per tablet). Smaller doses at multiple times per day may be preferred.

EXAMPLE

A male subject, age 43, was under treatment for uneasiness, short temper and prolonged anger, and was taking welbutrin. The subject suffered side effects of stomach discomfort, memory deficiency and reduced clarity of thought. The subject began taking three 500 mg tablets containing a 1:1 ratio of calcium/magnesium butyrate, twice per day, then 2 tablets 3 times per day. The subject reported comparable effects to WELLBUTRIN, controlling his chronic uneasiness, short temper and prolonged anger, with no side effects and in particular reported a significant improvement in short term memory, and decision making ability, with no stomach discomfort. The subject no longer uses WELLBUTRIN.

Example 2

40 g of magnesium oxide and 82 g of calcium hydroxide were added to 400 ml of water. While stirring, 370 g of butyric acid were added, the salts maintained at a temperature of about 70 degrees C. The pH was adjusted to about 7 and the mixture then cooled, the solids filtered, washed, dried and granulated.

The butyrate or an in vivo formed derivative appears to easily and readily transmigrate through the blood brain barrier, and exhibit an action of markedly increasing GABA in the brain. Subjects report a near immediate calming and clarity of thought after ingesting a dosage of the inventive compound, as well as an improvement in memory. Accordingly, the inventive compositions can be used as medicaments for the prevention and treatment of various impediments in cerebral function induced by a deficiency of GABA or altered GABA regulation of metabolism in the brain. Specifically, these compounds show an excellent efficacy in the adult symptoms associated with ADD and may have efficacy in the treatment of dementia attributed to cerebrovascular impediments and the like; dementia attributed to endocrine diseases and metabolic diseases such as hyperthyroidism, hypothyroidism, hyperparathyroidism, hypoparathyroidism, Wilson's disease, liver disease, hyperlipidemia, hypoglycemia, hypercalcemia, hypocalcemia, Cushing syndrome, hypopituitarism and uremia; dementia attributed to hypoxia such as cardiopulmonary diseases, anemia; dementia attributed to infectious diseases such as brain abscess, bacillary meningitis, tubercular meningitis, syphilis and cerebral helminthiasis, and dementia attributed to diseases of the central nervous system, such as Alzheimer-type senile dementia, Pick disease, Huntington disease and Parkinson disease. Many conditions, both physiological and/or psychological exhibit symptoms that may be treatable according to the present invention.

In using the butyrate of the invention for the prevention and treatment of impediments in cerebral function, their doses may vary widely depending upon the purpose of administration, the route of administration, the condition, body weight, age and sex of a person, the judgement of a physician treating the person, etc. Generally, in administration to humans, the doses are 0.01 mg/kg/day to 1,000 mg/kg/day, preferably 0.1 mg/kg/day to 100 mg/kg/day, more preferably 0.2 mg/kg/day to 50 mg/kg/day, either at one time or in several divided portions daily.

The route of administration may be oral or parenteral (e.g., intravenous, intraarterial, intramuscular, intraperitoneal, intramedullary, intrarectal), or transdermal.

For administration, the butyrate may be formulated into forms suitable for the above routes of administration, for example forms suitable for oral administration such as tablets, granules, powders, coated tablets, hard capsules, elastic capsules and syrups, or forms suitable for injection or intravenous drip infusion such as suspensions, solutions, or oily or aqueous emulsions.

Adjuvants normally used in formulating medicaments in the above-exemplified forms may equally be used as pharmaceutically acceptable liquid or solid diluents or carriers for formulating the compositions of this invention. Specific examples include syrup, gum Arabic, gelatin, sorbitol, tragacanth, polyvinyl pyrrolidone, magnesium stearate, talc, polyethylene glycol, silica, lactose, sucrose, corn starch, calcium phosphate, glycine, potato starch, carboxymethyl cellulose calcium, sodium laurylsulfate, water, ethanol, glycerol, mannitol, and a phosphate buffer, among others.

The butyrate of this invention may, if required, further contain other adjuvants customarily used in the field of pharmaceutical formulation, such as coloring agents, flavors, corrigents, antiseptics, dissolution acids, suspending agents and dispersing agents.

The butyrate may be in unit dosage forms such as tablets, capsules, coated tablets and ampoules mentioned above, or may be in a form contained in a multi-unit dosage receptacle.

The composition or agent, depending upon its form, etc., may contain the butyrate of the invention in a concentration of generally 0.01 to 50% by weight.

The following lists one exemplary composition, with possible ranges of these ingredients, according to the invention:

TABLE 1

Exemplary Dosage
4 Tablets

|  | Amount Per Dosage |  |
|---|---|---|
| Niacin | 20 mg | (0–30 mg) |
| Vitamin B-6 (Pyridoxine) | 30 mg | (0–40 mg) |
| Folic Acid | 60 mcg | (0–100 mg) |
| Vitamin B-12 (Cyanocobalamin) | 150 mcg | (0–200 mcg) |
| Calcium (from Calcium Butyrate) | 187 mg | (1–300 mg) |
| Magnesium (from Mag. Butyrate) | 161 mg | (1–300 mg) |
| Magnesium Butyrate | 1340 mg | (10–3000 mg) |
| Calcium Butyrate | 1050 mg | (10–3000 mg |
| Cordyceps (*Cordyceps sinensis* (Berk.) Sacc.) Aerial Parts | 450 mg | (0–600 mg) |
| L-Phenylalanine | 200 mg | (0–300 mg) |
| L-Taurine | 200 mg | (0–300 mg) |
| L-Tyrosine | 150 mg | (0–250 mg) |
| Phosphatidyl Serine | 150 mg | (0–250 mg) |
| L-Glutamine | 100 mg | (0–200 mg) |
| Ginkgo Biloba 24%/6% Leaf Extract | 90 mg | (0–150 mg) |
| Ginkgo Flavoneglycosides] | 22 mg | (0–70 mg) |
| Ginkgo Lactones | 5 mg | (0–10 mg) |
| Huperzia Serrata (*Huperzia serrata* (Thunb.) Trev.) Berry | 90 mg | (0–200 mg) |
| Lecithin (Soy) | 40 mg | (0–80 mg) |
| Phosphatidyl Choline | 8 mg | (0–20 mg) |
| Pregnenolone | 30 mg | (0–60 mg) |
| Choline Bitartrate | 20 mg | (0–60 mg) |
| Inositol | 20 mg | (0–30 mg) |
| Dibencozide (Cobamamide) | 60 mcg | (0–150 mg) |

The composition may further optionally contain hydroxypropylcellulose, Stearic Acid, Silica, Magnesium Stearate, Pyridoxine 5 Phosphate, and other ingredients commonly used in or with pharmaceutically suitable carriers. The exemplary dosage above is believed to supply the equivalent of 2042 mg of Butyric Acid from the Calcium and Magnesium Butyrates. Four tablets, twice a day, is recommended though this can vary from person to person.

The present invention comprises compounds and compositions of butyric acid salts, or derivatives or combinations thereof. The invention also comprises a method for using these compounds for the treatment of cognitive and/or emotional conditions in persons suffering from diverse conditions, the symptoms of these conditions being broadly characterized clinically as Disruptive Behavior Disorders and/or memory-reasoning disorders. The method specifically treats as a subset the symptoms associated with attention deficit disorder/hyperactivity disorder by administrating an effective amount of a butyrate as defined above. It may also be useful in treating autism, Tourette's, uncontrolled ticks, and raise the seizure threshold for individuals.

An "effective" amount represents an amount necessary to relieve or reduce the symptoms exhibited by a human susceptible to or suffering from disruptive behavior disorder or memory/reasoning disorders. The compounds described above are effective over a wide range of dosages. It is understood that the dosage may vary based upon the condition to be treated, its severity, the age, weight, and response of the individual person, and the chosen route of administration. Thus, the suggested dosage ranges are not intended to limit the scope of the invention in any way. For example, the composition may be administered transdermally, to provide delivery of the butyrate at from about 10–3000 mg. per day. The composition may also be formulated to provide delayed or controlled release, using enteric coating or other techniques known in the art.

Treating in accordance with the present invention may include the prophylaxis of the named condition, amelioration, elimination or attenuation of the condition but at least encompasses prophylaxis, amelioration, elimination or attenuation of the emotional and/or cognitive symptoms resulting from the condition.

The inventive method includes selectively promoting GABA activity in a human host comprising administering at least one butyrate to a human host in need of such treatment. Compounds of the invention do not exhibit significant side effects in the human host.

The compositions defined above are based on the butyric acid moiety and may comprise analogs, homologs, including next adjacent homologs, and compounds based on any of the foregoing. Analogs of butyric acid include both structural and functional analogs. Functional analogs are those compounds which are functionally related to the activity of butyric acid. Structural analogs are those compounds which are related to butyric acid in the arrangement or number of carbon atoms.

The butyrates, after introduction into the human host, may metabolize into active forms for increasing GABA in the brain and thus have the desired effect on the person taking it. Active compounds may also include those which metabolize in a time-release fashion to promote efficacy for long periods of time.

Another ingredient may be incorporated to increase bioavalability of the butyrate in the brain, such as ketoprofen, diflunisal, salsalate, etodolace, tolmetin, ibuprofen, naproxen, oxaprozin, salicylic acid, acetyl salicylic acid, indomethacin, flurbiprofen, diclofenal, mefenamic acid, meclofenamic acid, ketorolac, sulindac, valproic acid or 2-valproenic acid. Many of these are non-steroidal anti inflammatory drugs (NSAIDS) which may be referred to as beta-oxidation inhibitors. These may prolong the half-life of the compounds in a patient, to increase the effectiveness and/or duration of the butyrates, which may allow a lower dosage to obtain equivalent therapeutic effects.

Example

An adult male subject with ADD who had been taking WELLBUTRIN was tested and found to have a deficiency in α-GABA by plasma amino acid analysis. Upon taking 3 tablets, 2 times per day (500 mg tablets of mag/cal butyrate, 40/60 ratio) the subject noted a near immediate improved mood effect and reported a calming and clarity of thought not achieved by the prior treatments. The subject has continued to take the butyrate tablets and no longer uses WELLBUTRIN.

Another subject who had been a long term user of Ritalin, reported comparable results, and no longer uses Ritalin. A person suffering from mild autism and experiencing difficulty in concentrating and fidgeting was given a 250 mg. tablet formulated as above and reported a calming effect at least equivalent to other therapeutic treatments.

While preferred embodiments of the present invention have been shown and described, it will be understood by those skilled in the art that various changes or modifications can be made without varying from the scope of the present invention.

What is claimed is:

1. A formulation for treating symptoms of cognitive and/or emotional conditions consisting of difficulty in concentration, fidgeting, anger, memory deficiency, and clarity of thought, comprising at least one butyrate composed of at least one alkaline metal or alkaline earth metal salt of n-butyric acid, and at least one component selected from the group consisting of L-glutamine, 1-phenylalanine, 1-tyrosine and 1-taurine, in a pharmaceutically acceptable carrier.

2. The formulation of claim 1 wherein the salt is selected from the group consisting of lithium, sodium, potassium, calcium, magnesium, zinc and barium.

3. The formulation of claim 1 wherein the at least one butyrate is composed of calcium butyrate and magnesium butyrate.

4. The formulation of claim 3 wherein the calcium butyrate and magnesium butyrate are present in a ratio of from 10:90 to 90:10, respectively.

5. The formulation of claim 3 wherein about 1000 mg of calcium butyrate and about 1350 mg magnesium butyrate are present.

6. The formulation of claim 1 further comprising vitamin B6.

7. The formulation of claim 1 further comprising vitamin B12.

8. The formulation of claim 1 wherein the at least one butyrate is present at from 10–300 mg.

9. The formulation of claim 1 wherein the formulation is in a unit dosage form.

10. The formulation of claim 1 comprising from 10–3000 mg of the n-butyrate salt, and further comprising about 50–200 mg of vitamin B12, and about 2–20 mg vitamin B6.

11. The formulation of claim 1 further comprising about 10–100 mg of Ginkgo Biloba.

12. The formulation of claim 1 further comprising an oligomeric proanthocyanidin.

13. The formulation of claim 1 further comprising at least one ingredient selected from the group consisting of antioxidants, antidepressants, memory promoters, vitamins, nutritional supplements and herbal supplements.

14. A method for treating the symptoms of cognitive and emotional disorders consisting of difficulty in concentration, fidgeting, anger, memory deficiency and clarity of thought in an mammal in need of such treatment comprising administering to such mammal a therapeutically effective amount of a formulation containing at least one alkaline metal or alkaline earth metal salt of n-butyric acid.

15. The method of claim 14 wherein the formulation further comprises a pharmaceutically acceptable carrier.

16. The method of claim 14 wherein the formulation is a unit or multiple dosage form.

17. The method of claim 14 wherein the formulation is administered in an amount of from about 0.01 to about 1000 mg per kg body weight/day.

18. The method of claim 14 wherein the formulation is administered in an amount of 0.1 to 100 mg per kg body weight/day.

19. The method of claim 14 wherein the formulation is administered in an amount of from about 0.2 to about 50 mg per kg body weight/day.

20. The method of claim 14 wherein the formulation is composed of a salt selected from the group consisting of lithium, sodium, potassium, calcium, magnesium, zinc and barium.

21. The method of claim 14 wherein the formulation is composed of calcium butyrate and magnesium butyrate.

22. The method of claim 21 wherein the calcium butyrate and magnesium butyrate are present in a ratio of from 10:90 to 90:10, respectively.

23. The method of claim 21 wherein about 1000 mg of calcium butyrate and about 1350 mg magnesium butyrate are present.

24. The method of claim 14 wherein the formulation comprises from 10–3000 mg of the n-butyrate salt, and further comprising about 50–200 mg of vitamin B12, and about 2–20 mg vitamin B6.

25. The method of claim 14 wherein the formulation is administered orally.

26. The method of claim 14 wherein the formulation further comprises at least one ingredient selected from the group consisting of antioxidants, antidepressants, memory promoters, vitamins, nutritional supplements and herbal supplements.

* * * * *